(12) United States Patent  
Martinelli

(10) Patent No.: US 7,296,500 B1  
(45) Date of Patent: Nov. 20, 2007

(54) SYSTEM AND METHOD FOR APPLYING TORQUE TO A FASTENER

(75) Inventor: Scot Martinelli, San Diego, CA (US)

(73) Assignee: Nu Vasive, Inc., San Diego, CA (US)

( * ) Notice: Subject to any disclaimer, the term of this patent is extended or adjusted under 35 U.S.C. 154(b) by 0 days.

(21) Appl. No.: 11/333,834

(22) Filed: Jan. 17, 2006

Related U.S. Application Data

(60) Provisional application No. 60/644,418, filed on Jan. 15, 2005.

(51) Int. Cl.
*B25B 17/02* (2006.01)
*A61B 17/58* (2006.01)

(52) U.S. Cl. ...................... 81/57.29; 606/61
(58) Field of Classification Search .......... 81/57.29, 81/58.1, 467–483, 429, 55
See application file for complete search history.

(56) References Cited

U.S. PATENT DOCUMENTS

| | | | | |
|---|---|---|---|---|
| 2,752,809 A | * | 7/1956 | Lehmann | 81/55 |
| 2,790,343 A | * | 4/1957 | White | 81/55 |
| 3,139,675 A | * | 7/1964 | Devine et al. | 29/240 |
| 3,156,141 A | * | 11/1964 | Pluntz | 81/57.32 |
| 3,394,623 A | * | 7/1968 | Kinakin | 81/55 |
| 3,485,118 A | * | 12/1969 | Maughan, Jr. | 81/125 |
| 3,572,188 A | * | 3/1971 | Christian, Jr. | 81/57.46 |
| 3,889,558 A | * | 6/1975 | Duncan | 81/55 |
| 3,891,181 A | * | 6/1975 | Sanders | 251/128 |
| 4,165,660 A | * | 8/1979 | Behrens | 81/55 |
| 4,334,443 A | * | 6/1982 | Pearson | 81/55 |
| 4,573,378 A | * | 3/1986 | McDonald | 81/463 |
| 4,762,031 A | * | 8/1988 | Bradley | 81/57.22 |
| 5,052,249 A | * | 10/1991 | Go | 81/55 |
| 5,734,113 A | * | 3/1998 | Vogt et al. | 73/862.23 |
| 6,216,562 B1 | * | 4/2001 | Hsieh | 81/57.29 |
| 6,272,952 B1 | * | 8/2001 | Hsu et al. | 81/57.22 |
| 6,598,500 B1 | * | 7/2003 | Chivington | 81/55 |
| 6,634,260 B1 | * | 10/2003 | Smith | 81/57.36 |
| 6,872,208 B1 | * | 3/2005 | McBride et al. | 606/61 |
| 6,887,241 B1 | * | 5/2005 | McBride et al. | 606/61 |
| 7,100,476 B1 | * | 9/2006 | Feit | 81/57.29 |
| 2003/0213340 A1 | * | 11/2003 | Alden | 81/57.29 |
| 2004/0187651 A1 | * | 9/2004 | Amami | 81/467 |
| 2006/0089644 A1 | * | 4/2006 | Felix | 606/61 |
| 2006/0111712 A1 | * | 5/2006 | Jackson | 606/61 |

* cited by examiner

*Primary Examiner*—David B Thomas
(74) *Attorney, Agent, or Firm*—Jonathan Spangler

(57) ABSTRACT

A torque multiplication system having a mechanism for torque determination including an anti torque component, an input handle, a transfer mechanism, and an output shaft for use in setting screws in spinal surgery to a predetermined target torque.

20 Claims, 18 Drawing Sheets

SYSTEM AND METHOD FOR APPLYING TORQUE TO A FASTENER

CROSS REFERENCES TO RELATED APPLICATIONS

The present application is a non-provisional patent application claiming benefit under 35 U.S.C. § 119(e) from U.S. Provisional Application Ser. No. 60/644,418, filed on Jan. 15, 2005, the entire contents of which are hereby expressly incorporated by reference into this disclosure as if set forth fully herein.

BACKGROUND OF THE INVENTION

I. Field of the Invention

The present invention relates generally to applying torque to a fastener and, more particularly, to the measured tightening of a fastener in medical applications.

II. Discussion of the Prior Art

The use of surgical fixation systems involving screws is an accepted practice for a variety of orthopedic procedures. One procedure experiencing proliferated growth is that of spinal fixation, wherein surgical screws are bored into adjacent vertebral bodies and used to anchor rods to immobilize one or more spinal levels. Each screw generally comprises a shank for introduction into bone (such as a pedicle) and a housing or "tulip" coupled to the shank, either fixedly to form a "fixed axis screw" or adjustably to form a "multi-axis screw". In either event, the rod is received within the housing of the screw and a fastener is employed to secure the rod within or to the housing. One manner of tightening the fastener within or to the housing involves the use of a basic torque driver, such as a screwdriver dimensioned to drive the fastener into engagement with the screw housing.

Although generally effective, this basic torque driver is nonetheless disadvantageous in that a surgeon must apply the entire torque necessary to properly tighten the fastener. Another drawback of the existing systems is that, to the extent such basic torque drivers include meters or "read outs," such meters are challenging to read during the application of torque by the surgeon.

The present invention is directed at overcoming, or at least improving upon, the disadvantages of the prior art.

SUMMARY OF THE INVENTION

The present invention accomplishes this goal by providing a system and method for applying torque to a fastener, including a stationary anti-torque handle, a mechanism to multiply an input force and transfer the force to the output shaft, an input handle for generating the input force, and an output shaft to turn the screw (collectively "torque multiplier system"). As will be described in greater detail below, the torque multiplier system of the present invention advantageously supplies the operator with a greater mechanical advantage and thereby decreases the required torque input. It is also more stable than previous torque drivers and thereby offers a more accurate method of assuring that the torque requirement is met.

According to one broad aspect of the present invention, the anti-torque device may include any number of components capable of preventing rotation of the screw housing. By way of example only, the anti-torque device may include a shaft which mates at its distal end to the screw housing, and a handle coupled to the proximal end of the shaft for establishing leverage and stability when applying torque. The input handle will multiply the force input by the user and transfer it to the fastener along the output shaft. This input force can be generated in numerous fashions, including but not limited to the use of a rod in a ratcheting action or twisting a pistol grip handle. The transfer mechanism may include any number of components capable of conveying the input force along the output shaft to the screw. By way of example only, the transfer mechanism may include, but is not limited to, gears, pulleys, or levers.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The torque multiplication system disclosed herein boasts a variety of inventive features and components that warrant patent protection, both individually and in combination.

Moreover, although described herein within the context of spinal fixation procedures, it will be readily appreciated by those skilled in the art that the torque multiplication system of the present invention may be employed in any number of suitable procedures without departing from the scope of the present invention.

Figure 20:
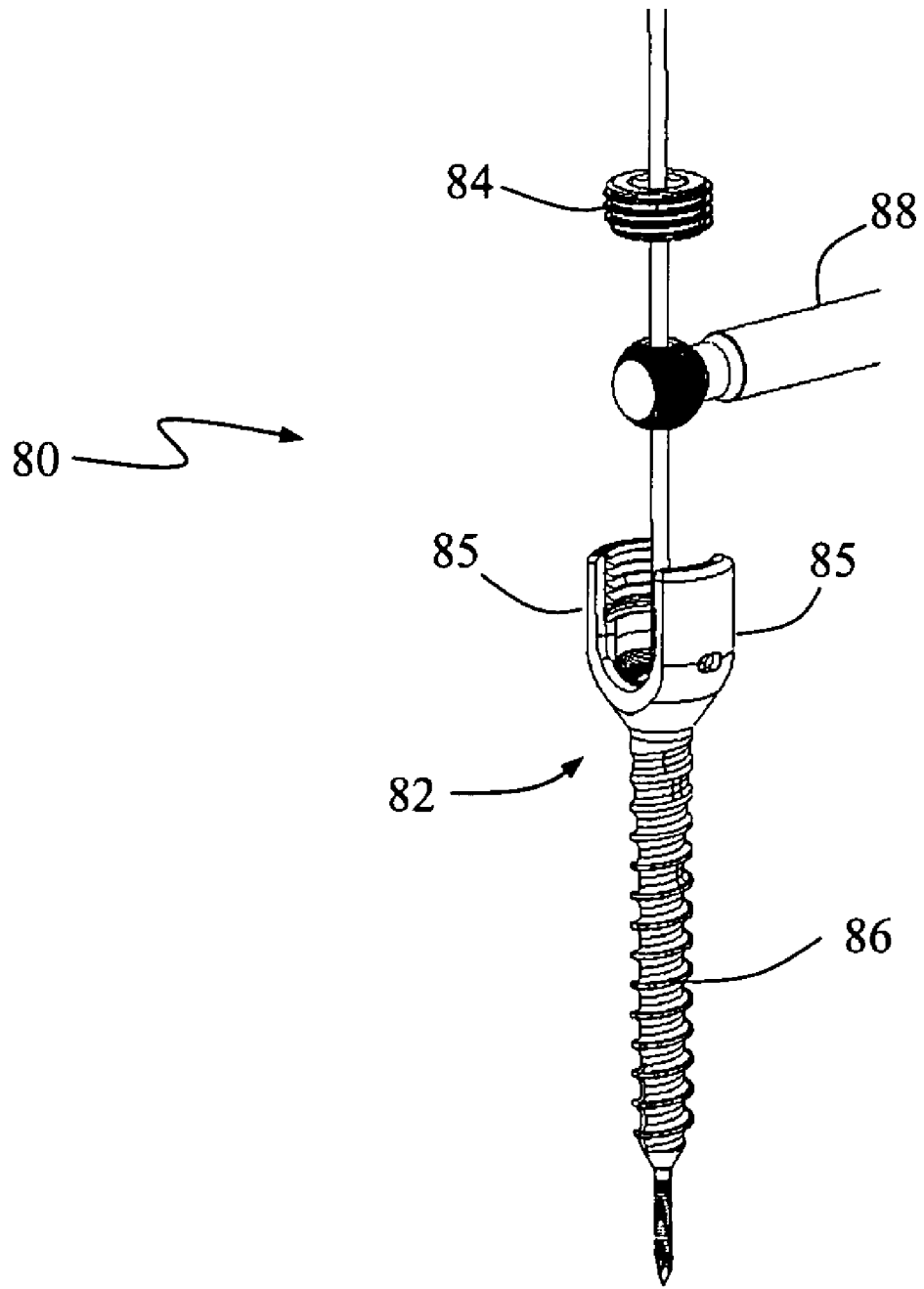
FIG. 20 is an exploded side view of one example of a pedicle screw system with which the torque multiplication system of the present invention may be adapted to be used.

FIGS. 1-11 illustrate an example of a torque multiplication system 10 according to one embodiment of the present invention in use with a pedicle screw system 80. Referring to FIGS. 1-5, the torque multiplication system 10 includes an anti-torque component 12, a torque input handle 14, a torque transfer mechanism 16, and an output shaft 18. As will be discussed in further detail below, the torque multiplication system 10 of the present invention may be used to apply a torque to a fastener, which (by way of example only) may be a setscrew 84 of the pedicle screw system 80 shown generally in FIGS. 1-2 and in further detail in FIG. 20). To do so, the pedicle screw system 80 (comprising a screw shank 86, a screw housing 82, setscrew 84, and a linking rod 88) is first positioned at the target site. The screw shank 86 is first implanted into the bone until a desired depth is achieved, for example at the point where the screw housing 82 is generally flush with the bone surface. The linking rod 88 is then placed within the screw housing 82 and the setscrew 84 is thereafter screwed over the rod 88.

The torque multiplier system 10 is then coupled to the pedicle screw system 80. This is accomplished by coupling the distal end 20 of the anti-torque component 12 to the screw housing 82. The distal end 21 of the output shaft 18 (shown in FIG. 10), which is coupled to the input handle 14 and transfer mechanism 16, is then coupled to the setscrew 84. While holding the stabilizing handle 13 of the anti-torque component 12 in one hand, the user would then rotate the input handle 14 about an axis parallel to the length of the input handle 14 to create torque. The torque created by rotating the input handle 14 is conveyed to the output shaft 18 via the transfer mechanism 16. This conveyance causes the output shaft 18 to rotate which consequently causes rotation of the setscrew 84. The setscrew 84 compresses the linking rod 88 into the screw housing 82 of the pedicle screw system 80. This compression will lock the pedicle screw system in place relative to the screw shank 86, thereby providing stabilization to the pedicle screw system 80.

Figure 1:
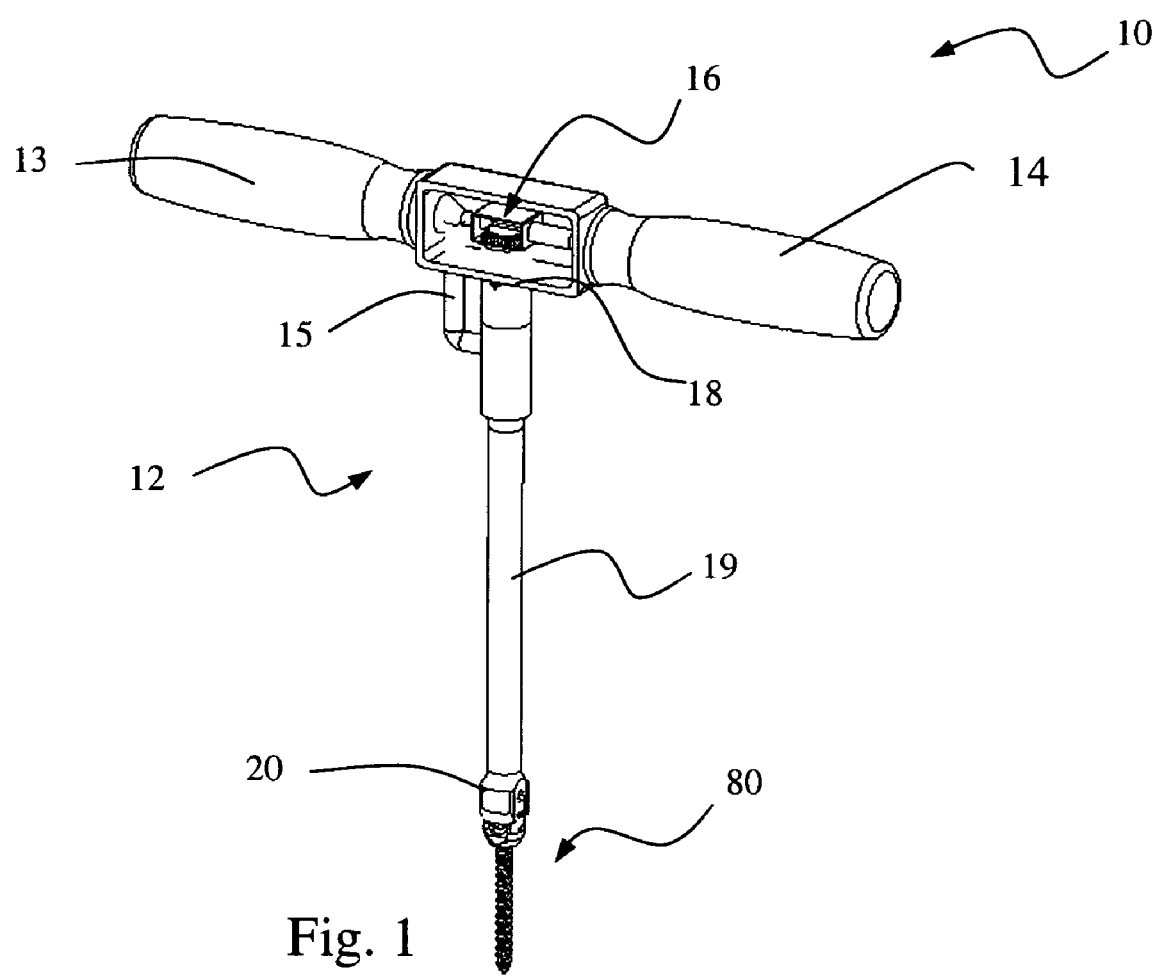
FIGS. 1-2 are perspective and front views, respectively, of a torque multiplication system according to one embodiment of the present invention.
Figure 2:
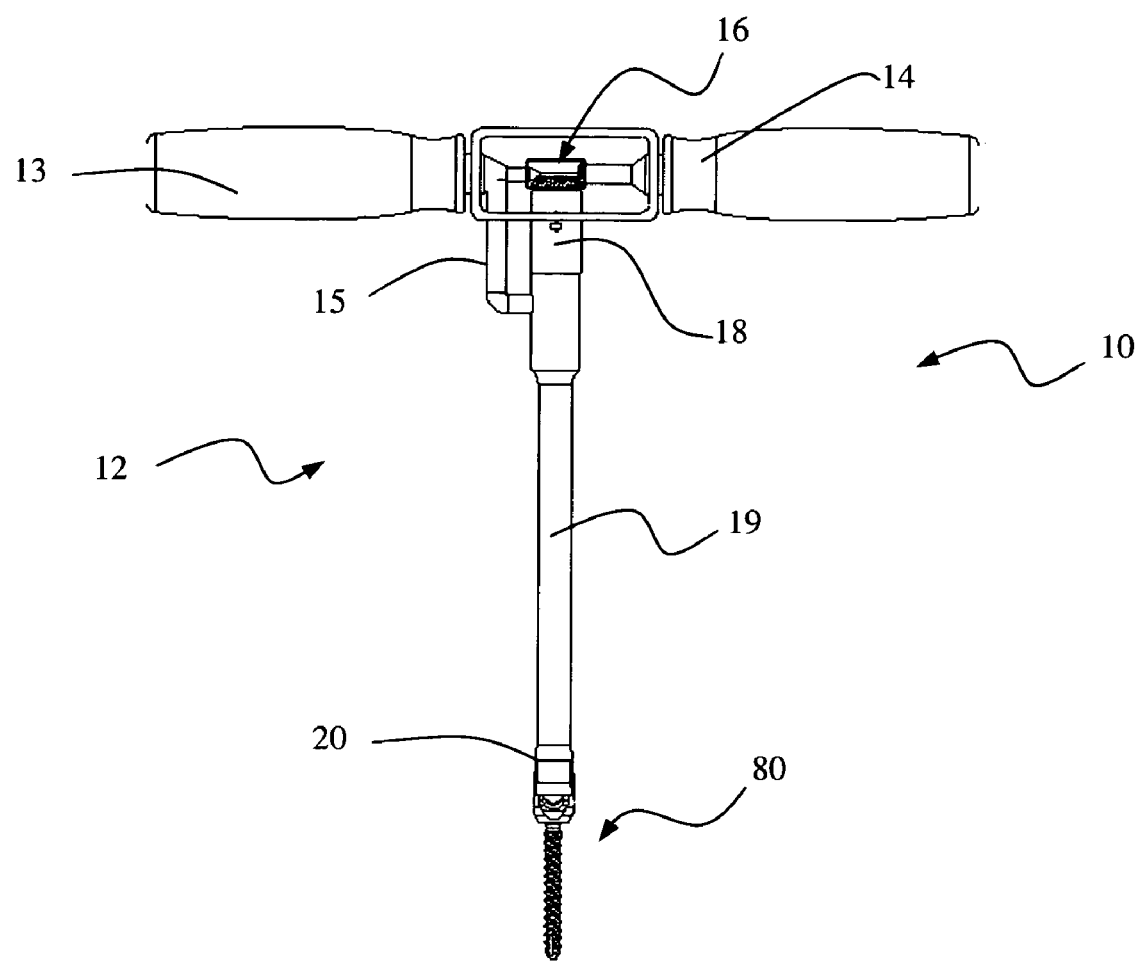
Figure 3:
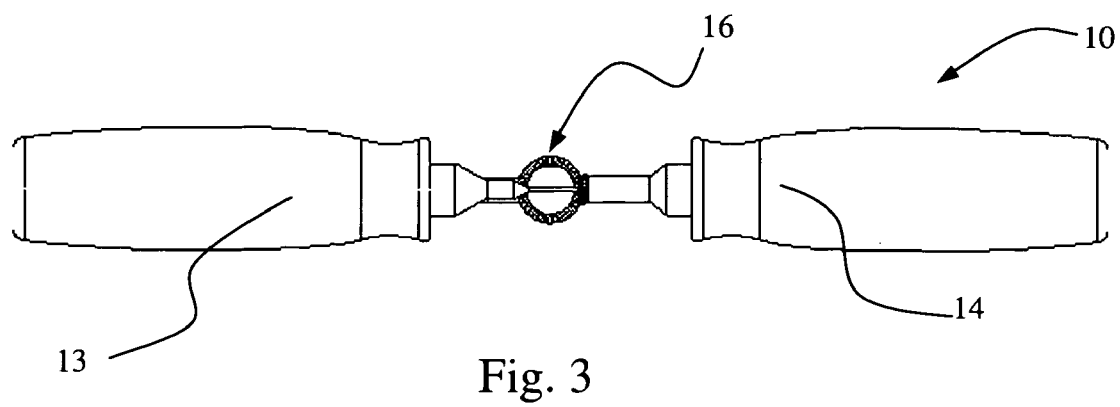
FIGS. 3-4 are top and side views, respectively, of the torque multiplication system of FIG. 1.
Figure 4:
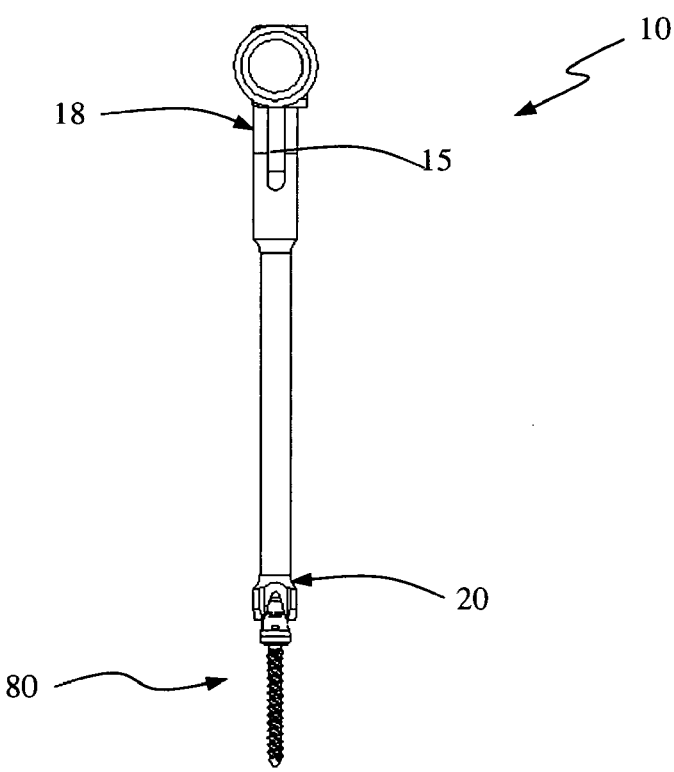
Figure 5:
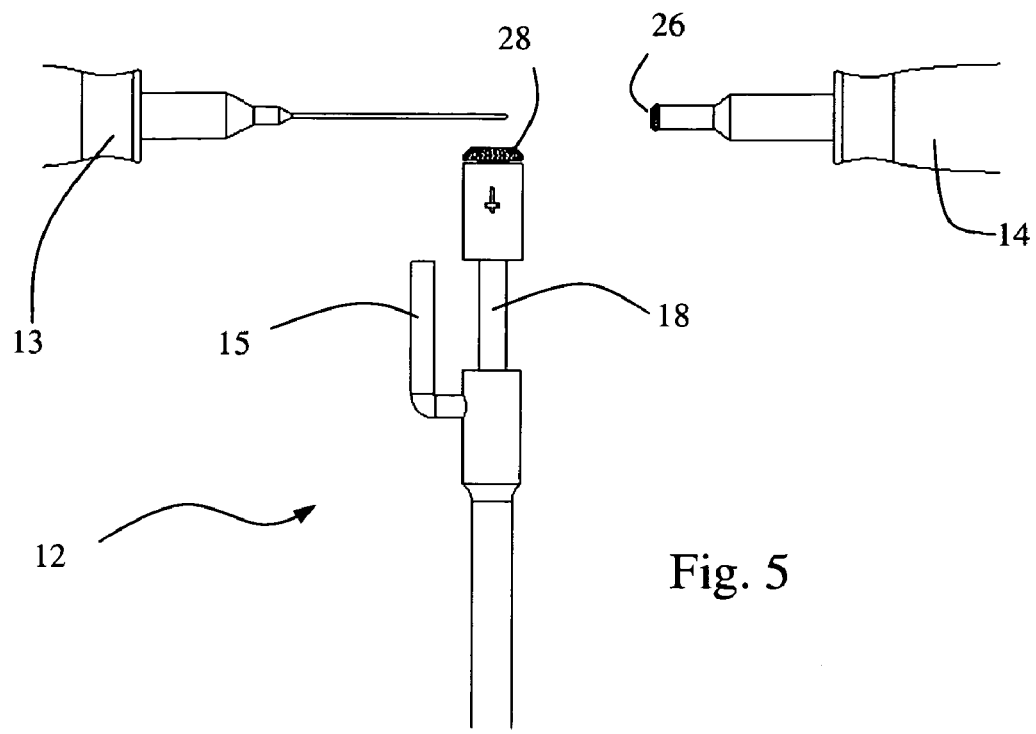
FIG. 5 is an exploded view of the torque multiplication system of FIG. 1.
Figure 6:
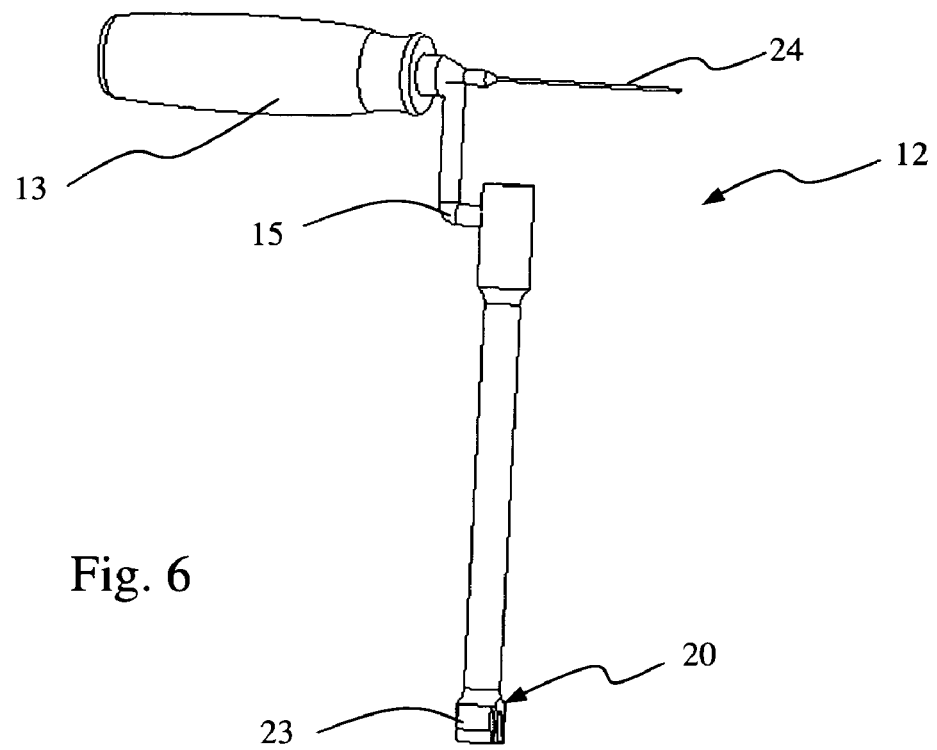
FIGS. 6-7 are perspective and front views, respectively, of an anti-torque component forming a part of the torque multiplication system of FIG. 1.
Figure 7:
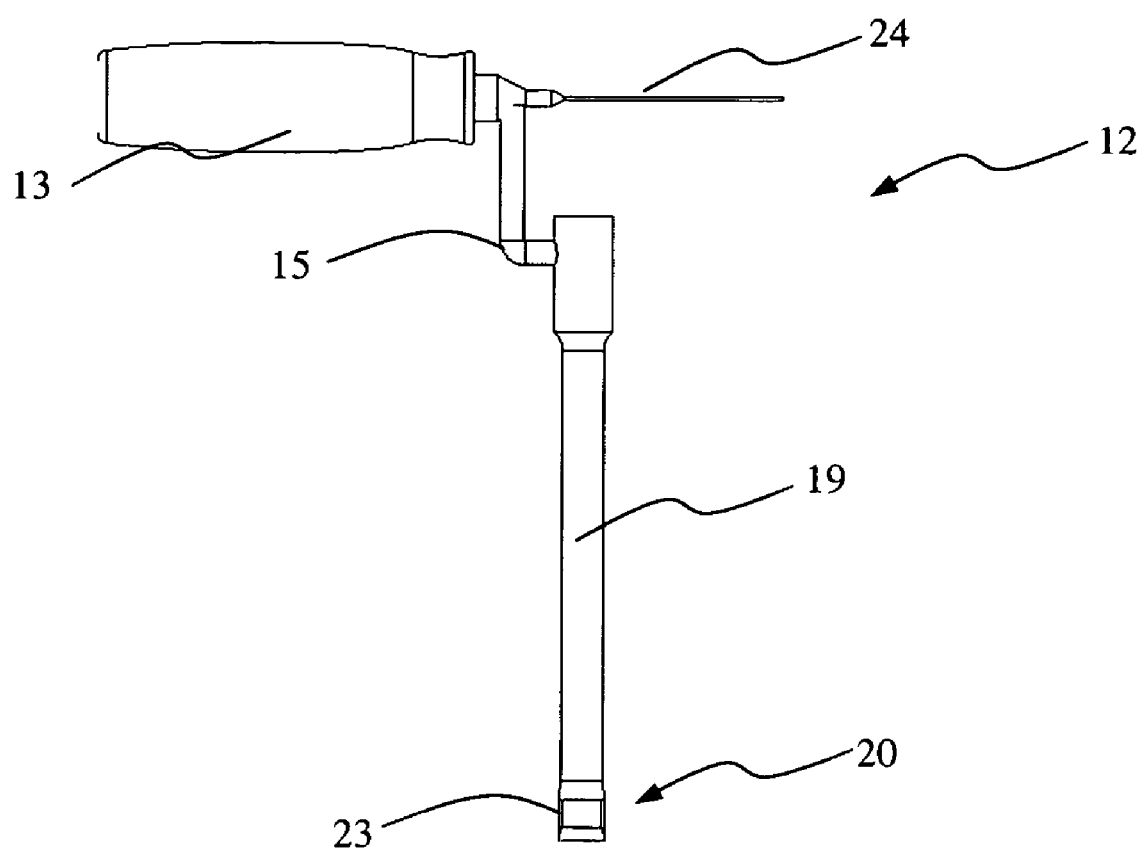

FIGS. 6-7 illustrate the anti-torque component 12 forming part of the torque multiplier system 10 described above. The anti-torque component 12 comprises a stabilizing handle 13, a joining member 15, and a tubular shaft 19 which collectively prevent rotation of the torque multiplication system 10 during use. The stabilizing handle 13 contains a stabilizing axle 24 extending into the input handle 14, thereby providing stability to the input handle 14 as torque is applied. The tubular shaft 19 is a hollow, elongated shaft dimensioned to receive the output shaft 18, described in further detail below. The distal end 20 of the tubular shaft 19 is dimensioned to interact with the housing 82 of the pedicle screw system 80. To accomplish this, distal end 20 contains a pair of wings 23 extending in a distal direction from the distal end 20. The wings 23 are dimensioned to mate with the wings 85 of the screw housing 82. By way of example only, this mating is accomplished by positioning the wings tubular shaft 19 such that the wings 85 of the screw housing 82 are received in between the wings 23 of the distal end 20 of the tubular shaft 19. The wings 23 may be provided having any number of peripheral profiles depending upon the peripheral profile of the wings 85 of the screw housing 82, including but not limited to the generally rectangular peripheral shape as shown. The tubular shaft 19 is connected to the stabilizing handle 13 through a joining member 15. The joining member 15 is generally located near a proximal end of the tubular shaft 19 may be provided having any number of suitable formations capable of bridging the gap between the tubular shaft 19 and the stabilizing handle 13, including but not limited to (and by way of example only), generally angled, generally arcuate, and generally straight.

Figure 8:
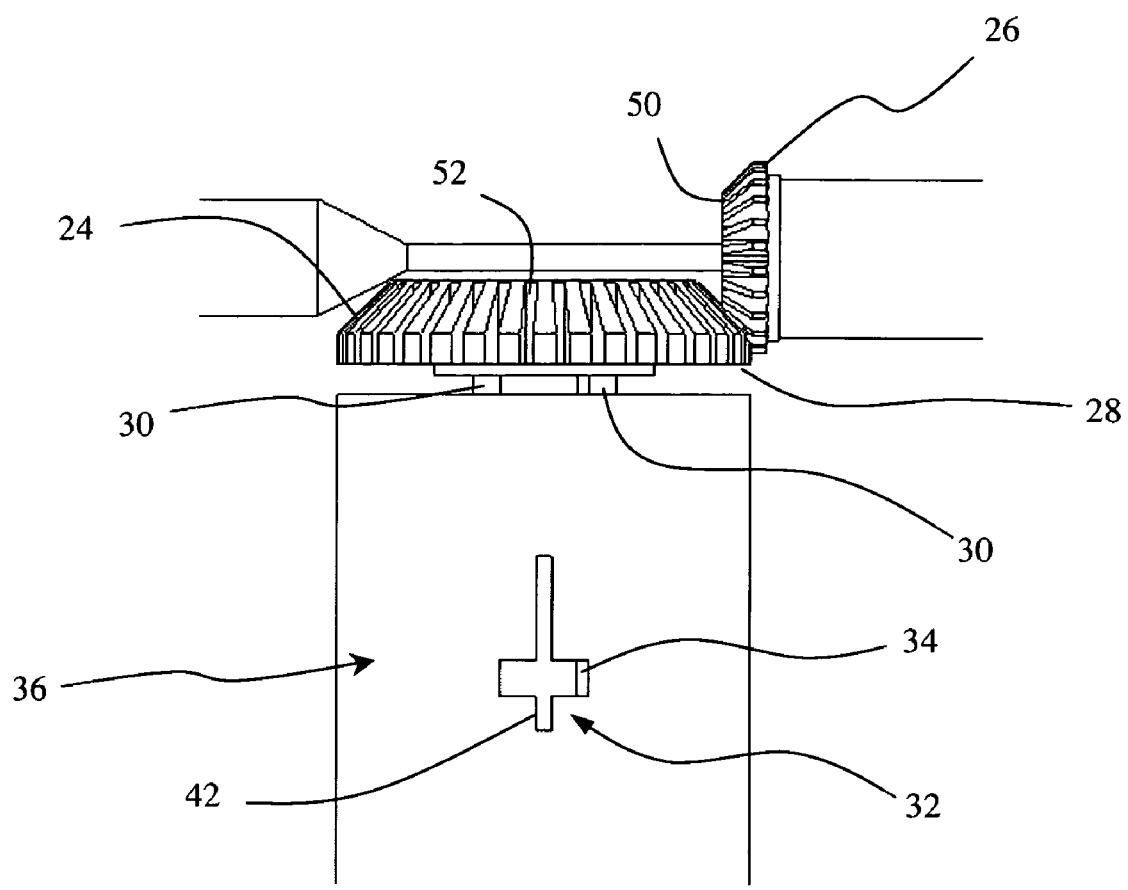
FIGS. 8-10 are front views of a transfer mechanism forming part of the torque multiplication system of FIG. 1.

FIGS. 8-11 illustrate the torque transfer mechanism 16 and the output shaft 18 of the torque multiplication system 10. Referring to FIG. 8, the torque transfer mechanism 16 includes a first gear 26, a second gear 28, and a plurality of torsion beams 30. The first gear 26 is located at a medial end of the input handle 14. By way of example only, the first gear 26 is generally circular in shape and has a plurality of radial grooves 50 distributed about its circumference. The second gear 28 is located at a proximal end of the output shaft 18, and is connected to the output shaft 18 by a plurality of torsion beams 30 that extend distally from the second gear 28 through the cylindrical cover 36 to the base surface 38 of the output shaft 18. By way of example only, the second gear 28 is generally circular in shape and has a plurality of radial grooves 52 distributed about its circumference. Grooves 50, 52 are dimensioned to interact with each other such that first and second gears 26, 28 cooperate (e.g. by forming a bevel gear) to effect a transfer of torque from the input handle 14 (by way of the first and second gears 26, 28 and torsion beams 30) to the output shaft 18.

Figure 9:
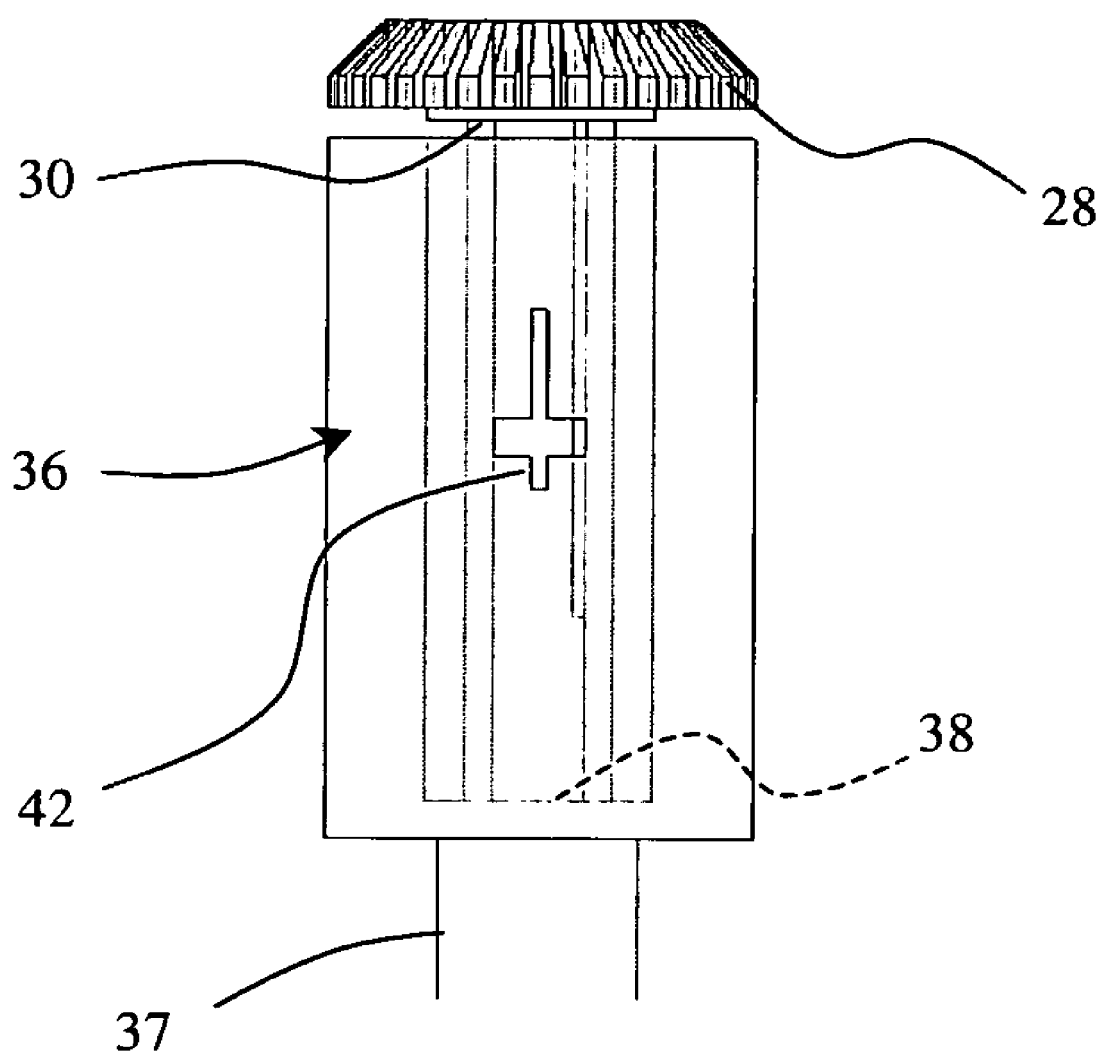
Figure 10:
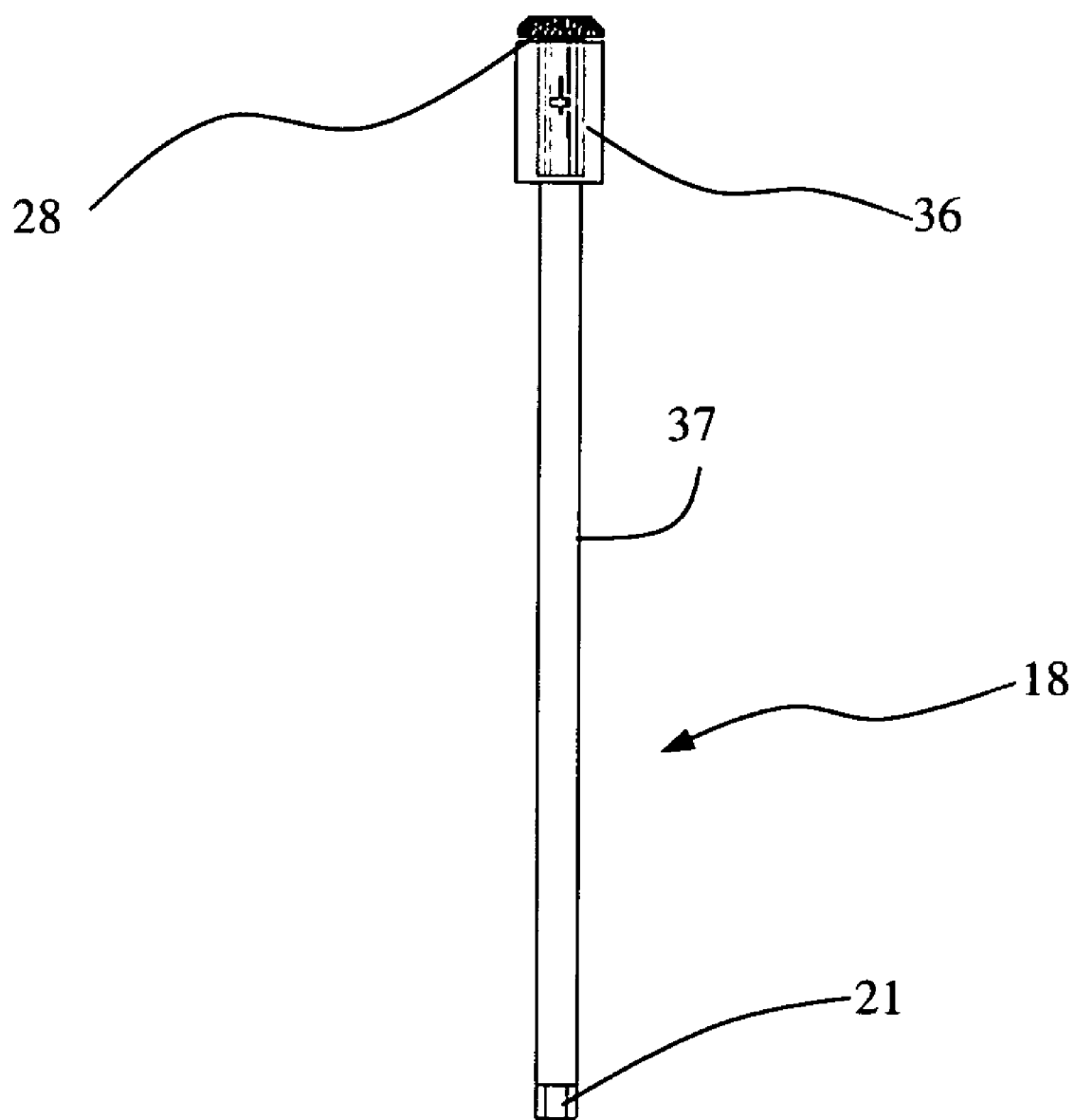
Figure 11:
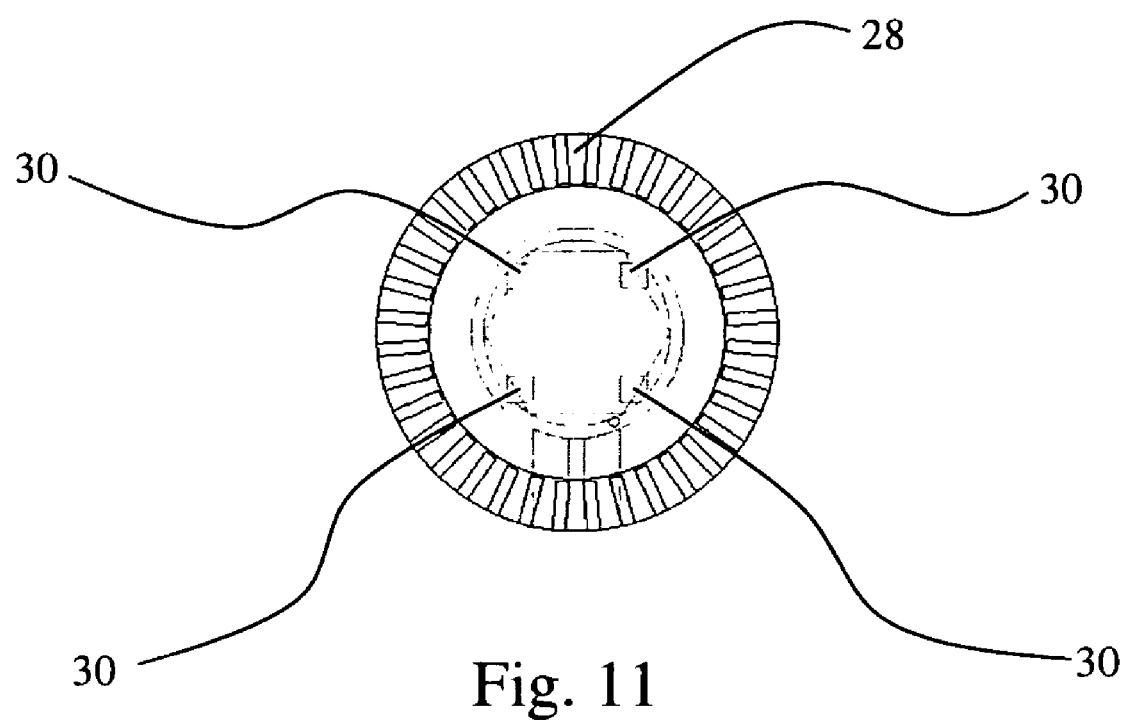
FIG. 11 is a top view of the transfer mechanism of FIG. 8.
Figure 12:
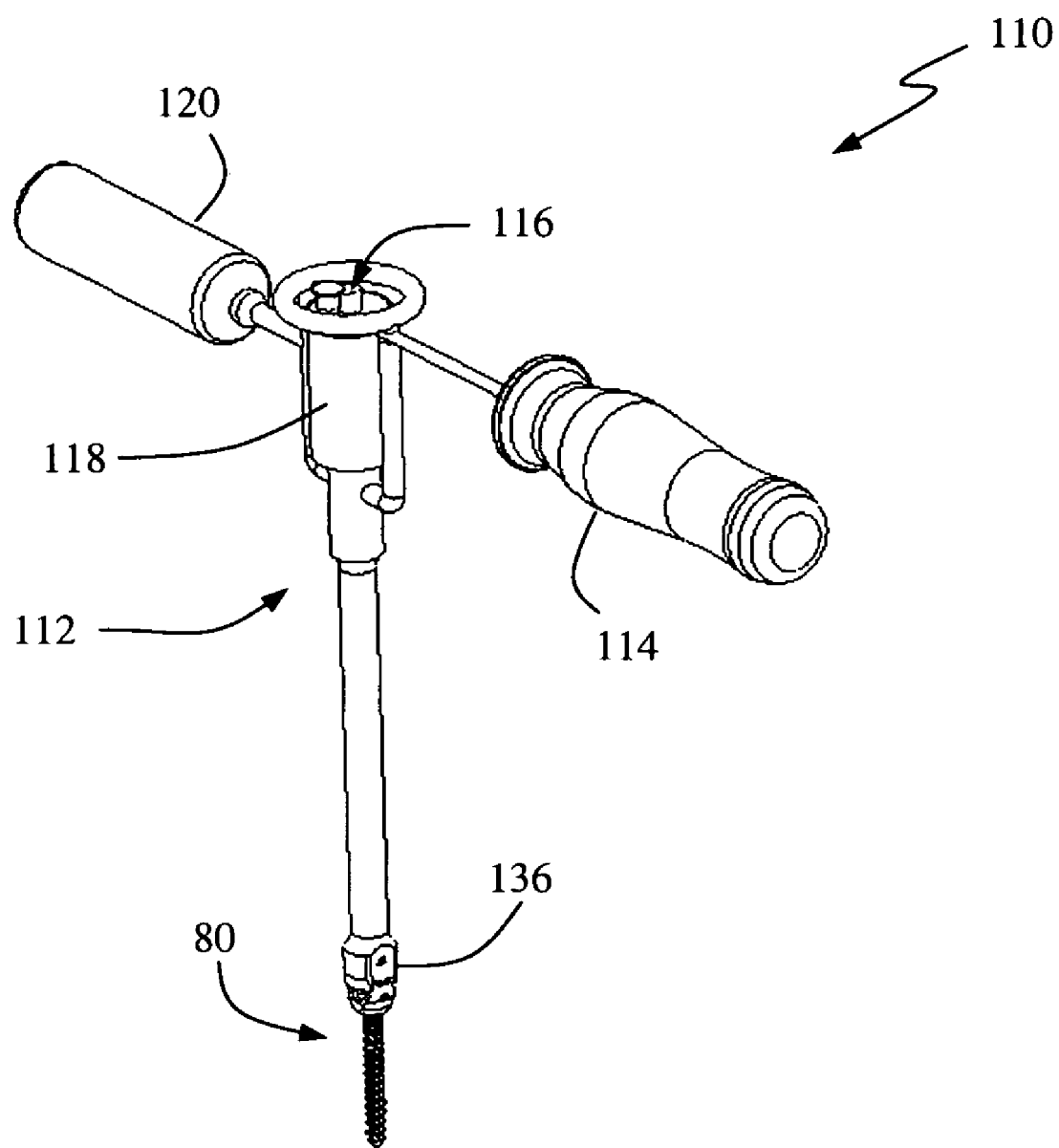
FIGS. 12-14 are perspective, front, and top views, respectively, of a torque multiplication system according to an alternative embodiment of the present invention.
Figure 13:
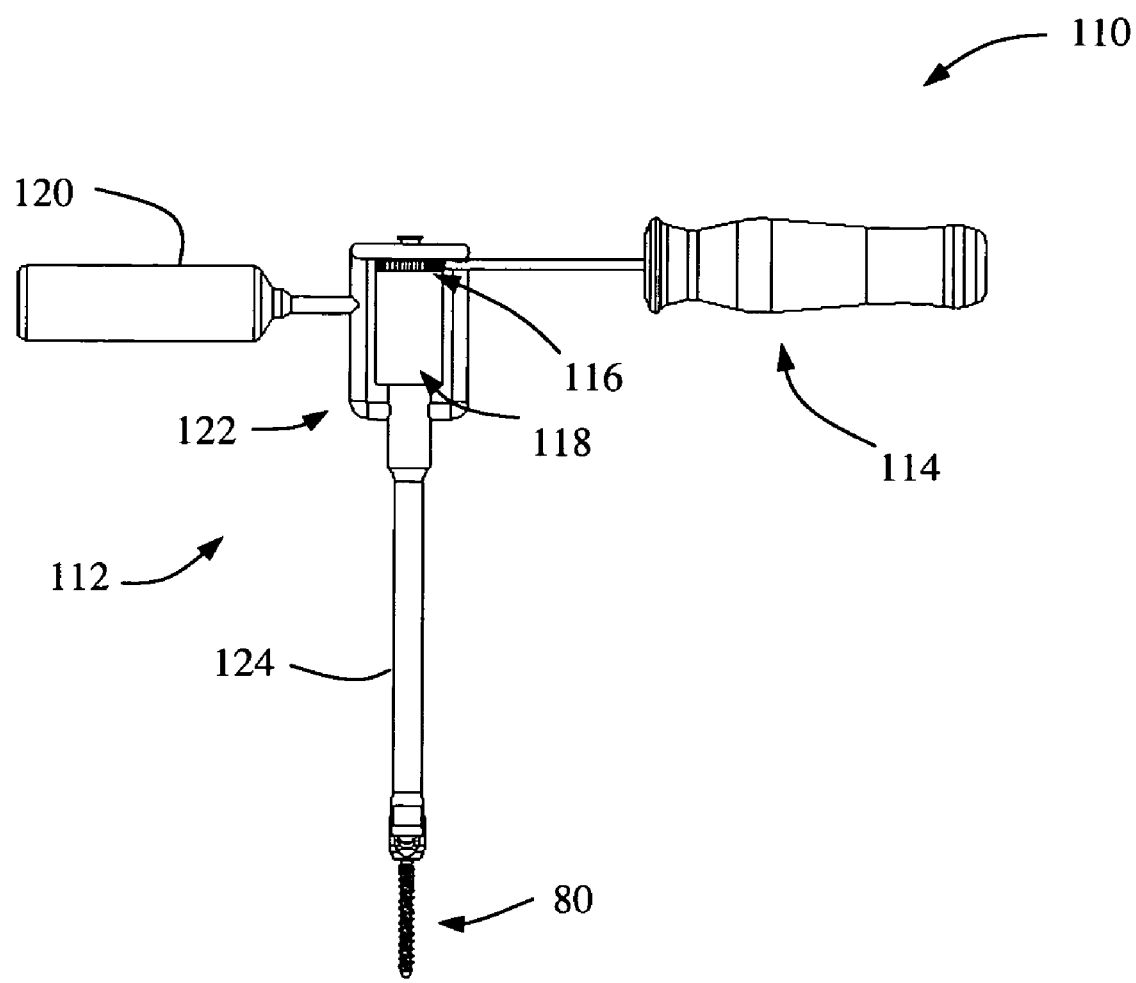
Figure 14:
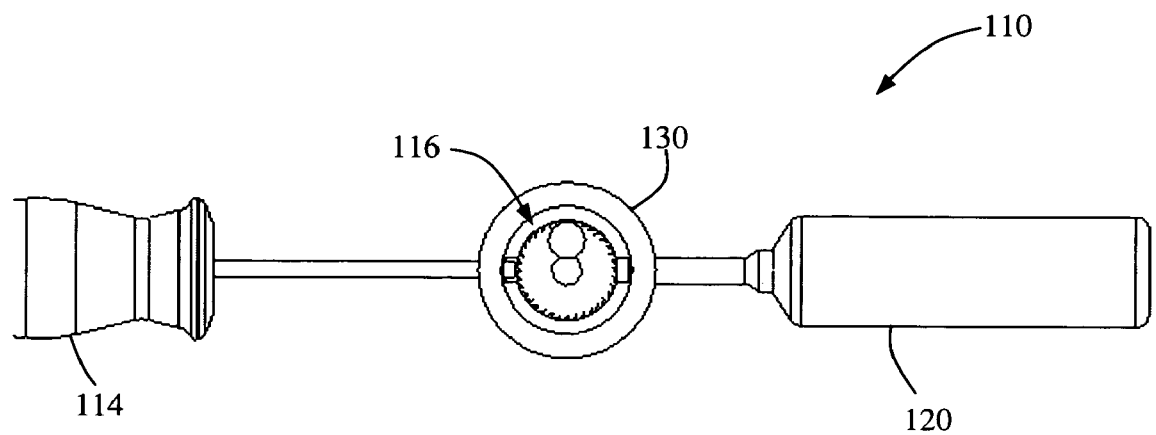

Referring to FIGS. 9-10, the output shaft 18 includes a cylindrical cover 36 at a proximal end and an engagement head 21 at a distal end. The cylindrical cover 36 includes a base surface 38 from which an elongated cylindrical protrusion 37 extends distally to the engagement head 21. As previously mentioned, the second gear 28 is located at a proximal end of the output shaft 18. A torque indicator 34 is connected to the second gear 28. The torque indicator 34 extends towards the base surface 38 and rotates with the second gear 28 when the input handle 14 is activated. When the second gear 28 rotates, the torsion beams 30 begin to deflect, and the indicator 34 continues to twist. The deflection of the torque indicator 34 can be seen through an indicator window 32 in the cylindrical cover 36. When the torque indicator 34 has deflected to the vertical torque window 42, the desired torque has been achieved.

FIGS. 12-19 illustrate an example of a torque multiplication system 110 according to an alternative embodiment of the present invention. Referring to FIGS. 12-16, the torque multiplication system 110 includes an anti-torque component 112, a torque input handle 114, a torque transfer mechanism 116, and an output shaft 118. The anti-torque component 112 includes a stabilizing handle 120 a joining region 122, and a tubular shaft 124 which collectively prevent rotation of the torque multiplication system 110 during use. The stabilizing handle 120 extends generally laterally from the joining region 122 and is connected to the output shaft 118 by the joining region 122. The joining region 122 includes a first joining member 126, a second joining member 128, and a stabilizing element 130. The output tubular shaft 124 is a hollow, elongated shaft dimensioned to received the output shaft 118 as detailed below.

The first joining member 126 is configured to connect the proximal end of the tubular shaft 124 to a medial end of the stabilization handle 120. The first joining member 126 may be provided having any number of suitable formations capable of bridging the gap between the stabilization handle 120 and the tubular shaft 124, including but not limited to (and by way of example only), generally angled, generally arcuate, and generally straight. The second joining member 128 is configured to connect the proximal end of the tubular shaft 124 to a medial end of the input handle 114. To accomplish this, the second joining member 128 includes a gap 132 having an engagement structure 134 (e.g., a pin) extending therein. The gap 132 is dimensioned to movably receive the medial end 146 of the elongated rod 142 of the input handle 114, as will be described further below. The second joining member 128 may be provided having any number of suitable formations capable of bridging the gap between the input handle 114 and the tubular shaft 124, including but not limited to (and by way of example only), generally angled, generally arcuate, and generally straight. The joining region 122 further includes a stabilizing element 130 configured to provide stability to the joining region 122 by attaching to each of the first and second joining members 126, 128. By way of example only, the stabilizing element 130 is shown as having a generally ringed shape, but it is contemplated that the stabilizing element 130 may have any geometric shape, including but not limited to generally circular and generally polygonal.

The distal end 136 of the tubular shaft 124 is dimensioned to interact with the housing 82 of the pedicle screw system 80. To accomplish this, distal end 136 contains a pair of wings 138 extending in a distal direction from the distal end 136. The wings 138 are dimensioned to mate with the wings 85 of the screw housing 82. By way of example only, this mating is accomplished by positioning the wings tubular shaft 124 such that the wings 85 of the screw housing 82 are received in between the wings 138 of the distal end 136 of the tubular shaft 124. The wings 138 may be provided having any number of peripheral profiles depending upon the peripheral profile of the wings 85 of the screw housing 82, including but not limited to the generally rectangular peripheral shape as shown. The tubular shaft 124 is connected to the stabilizing handle 120 through the joining member 122 as described above.

The torque input handle 114 includes a gripping member 140 positioned towards a lateral end of an elongated rod 142. The torque input handle 114 further includes an engagement feature 144 (e.g. an aperture configured to receive a pin) located near the medial end 146 of the elongated rod 142. The engagement feature 144 is dimensioned to movably engage with the engagement structure 134 located on the second joining member 128 such that the engagement structure 134 may act as a fulcrum and the torque input handle 114 may act as a lever (e.g. a ratchet crank handle). A gear-engagement feature 148 is provided at the medial end 146 of the elongated rod 138, and is dimensioned to interact with the gear 156 of the torque transfer mechanism 116, as described below.

Figure 17:
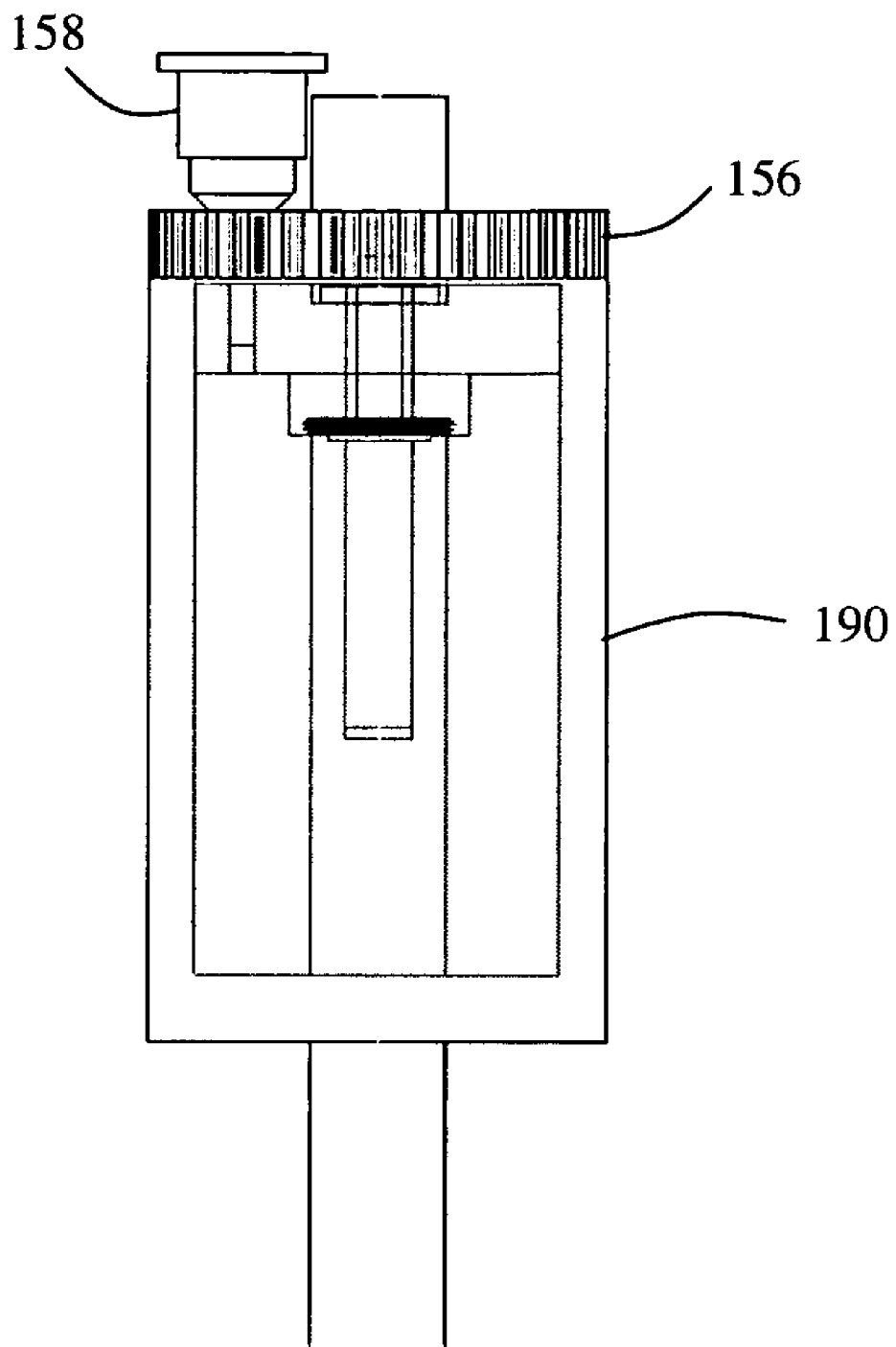
FIG. 17 is a front view of a transfer mechanism forming part of the torque multiplication system of FIG. 12.
Figure 18:
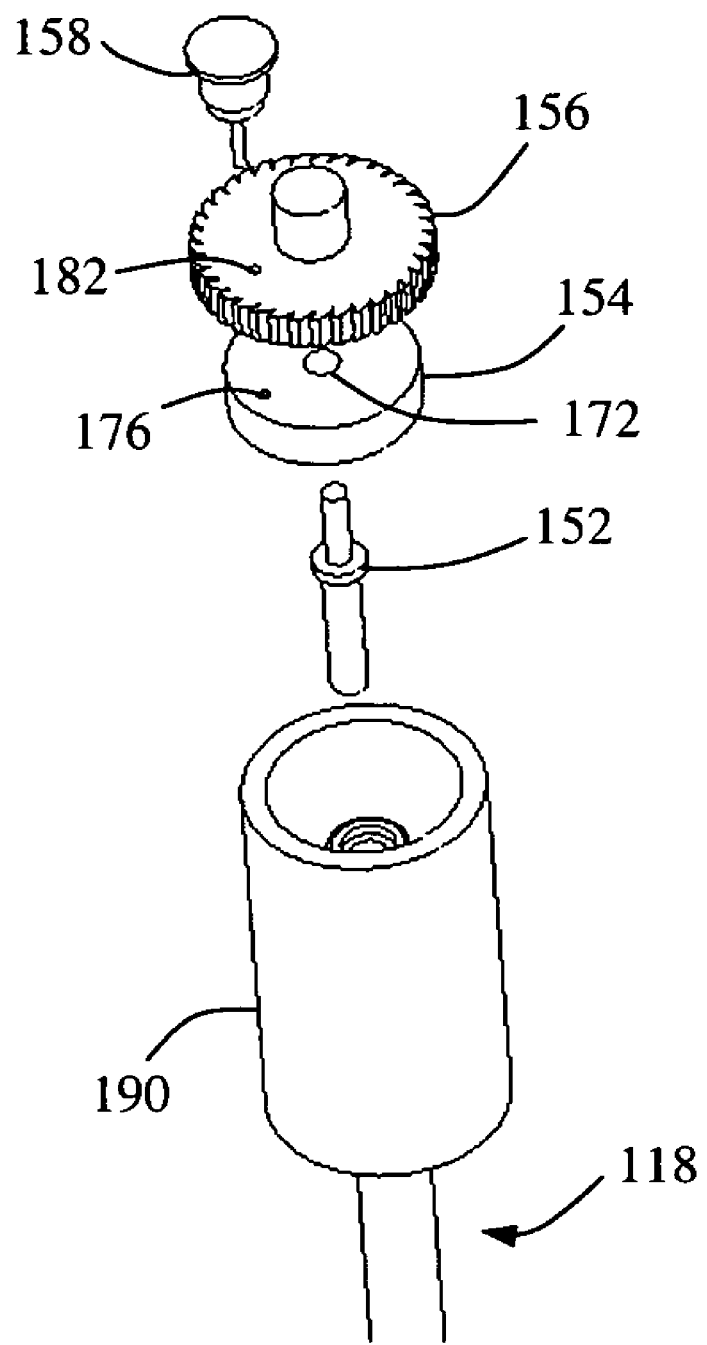
FIG. 18 is an exploded perspective view of the transfer mechanism of FIG. 17.
Figure 19:
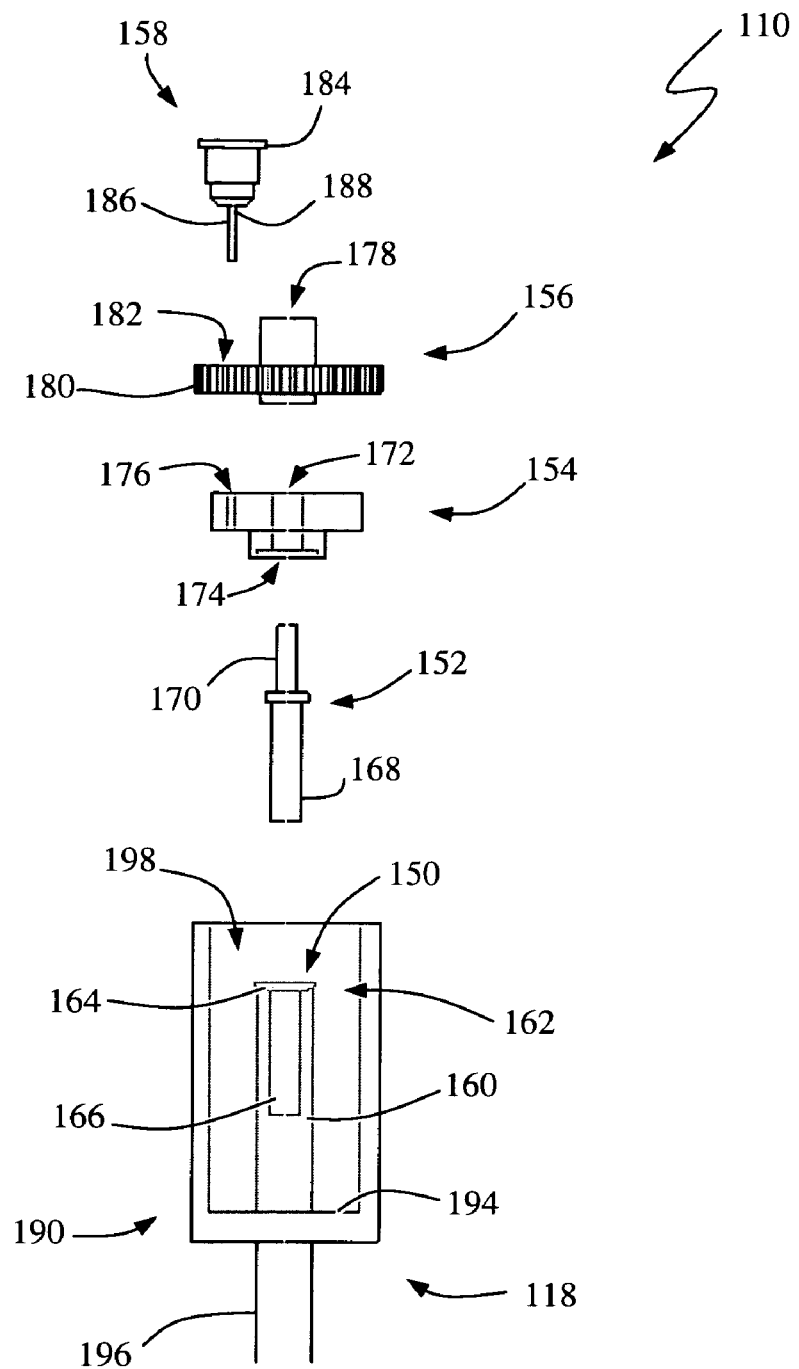
FIG. 19 is an exploded front view of the transfer mechanism of FIG. 17.

FIGS. 17-19 illustrate the torque transfer mechanism 116 and the output shaft 118 in greater detail. The torque transfer mechanism 116 includes an inner cylinder 150, a transfer axle 152, a shearing disk 154, a gear member 156, and a shear pin 158. The inner cylinder 150 includes an elongated portion 160 that extends in a proximal direction through the cylindrical cover 190 to a base surface 194 of the output shaft 118. The proximal end 162 of the inner cylinder 150 is provided with threads 164 dimensioned to interact with the shearing disk 154, as described below. The inner cylinder 150 is further provided with a hollow portion 166 dimensioned to receive the transfer axle 152.

The transfer axle 152 is provided as a generally elongated member having a distal portion 168 and a proximal portion 170. The distal portion 168 of the transfer axle 152 is dimensioned to be rotatably received within the hollow portion 166 of the inner cylinder 150. The proximal portion 170 is dimensioned to be rotatably received within the central bore 172 of the shearing disk 154, described in further detail below.

The shearing disk 154 is generally cylindrical in shape and dimensioned to snugly fit within the inner cavity 198 of the cylindrical cover 190 of the output shaft 118. The shearing disk 154 includes a central bore 172 dimensioned to receive the proximal portion 170 of the transfer axle 152. The central bore 172 may further include a threaded region 174 dimensioned to engage the threads 164 of the inner cylinder 150 such that the shearing disk 154 is rendered stationary in relation to the inner cylinder 150 (and thus the output shaft 118). The shearing disk 154 is further provided with a first aperture 176 dimensioned to receive the shaft 186 of the shear pin 158.

The gear member 156 is generally cylindrical in shape and includes a central bore 178 dimensioned receive at least a portion of the proximal portion 170 of the transfer axle 152. The gear member 156 is further configured to rest on top of both the shearing disk 154 and the cylindrical cover 190 of the output shaft 118. The gear member 156 is provided with a plurality of radial grooves 180 distributed about its circumference. The radial grooves are dimensioned to interact with the gear-engagement feature 148 of the input handle 114. The gear member 156 is further provided with a second aperture 182 dimensioned to align with the first aperture 176 of the shearing disk 154, and to receive the shaft 186 of the shear pin 158.

The shear pin 158 includes a head 184, a shaft 186, and a breakaway region 188 located generally near the interface of the head 184 and shaft 186. The shaft 186 is dimensioned to be inserted through the first and second apertures 176, 182 of the shearing disk 154 and rotating gear 156, respectively. The head 184 is adapted to snap off the shaft 186 at the breakaway region 188 upon application of a predetermined amount of torque to the input handle 114.

Figure 15:
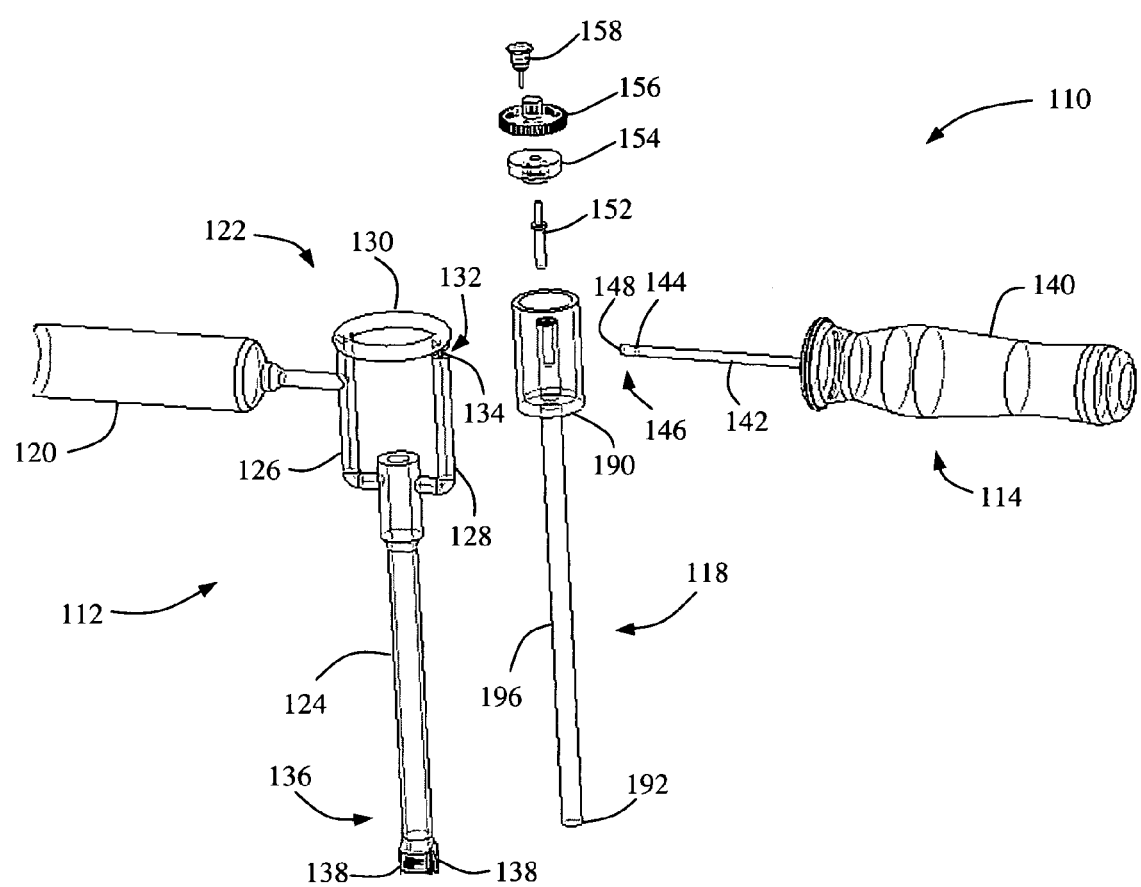
FIG. 15 is an exploded perspective view of the torque multiplication system of FIG. 12.
Figure 16:
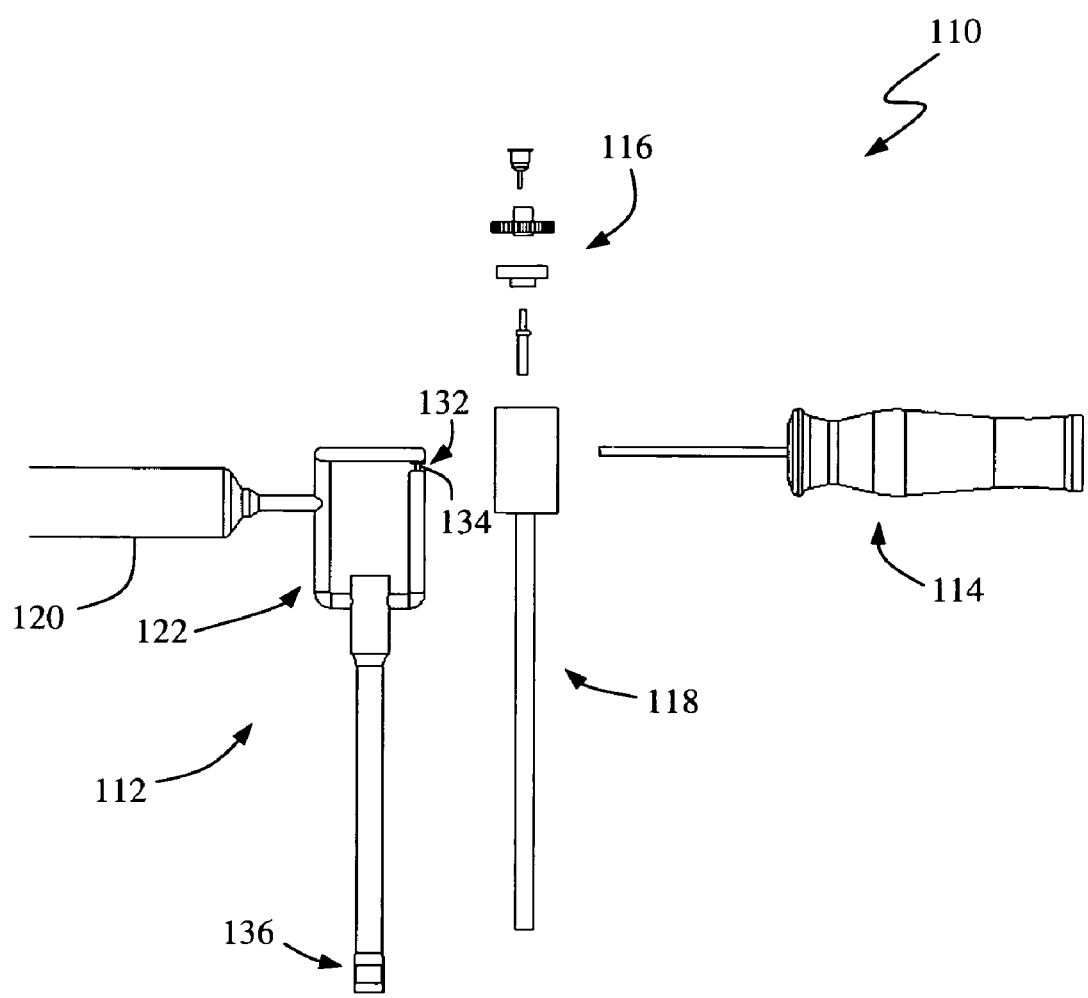
FIG. 16 is an exploded front view of the torque multiplication system of FIG. 12.

The output shaft 118 includes a cylindrical cover 190 at a proximal end and an engagement head 192 at a distal end (shown in FIG. 15). The cylindrical cover 190 includes a base surface 194 from which an elongated cylindrical protrusion 196 extends distally to the engagement head 192. The cylindrical cover 190 includes an inner cavity 198, wherein the inner cylinder 150 of the torque transfer mechanism 116 is located.

In use, the shaft 186 of the shear pin 158 is inserted into the first and second apertures 176, 182 of the shearing disk 154 and the gear member 156, respectively, such that the shearing disk 154 and the gear member 156 are temporarily stationary relative to one another. Due to the treaded engagement of the shearing disk 154 and the inner cylinder 150, the gear member 156 is effectively stationary relative to the distal end 192 of the output shaft 118. Once the shear pin 158 is in place, the torque multiplier system 110 is coupled to the pedicle screw system 80 in a similar fashion as to that described above in relation to torque multiplier system 10. This is accomplished by coupling the distal end 136 of the anti-torque component 112 to the screw housing 82. The distal end 192 of the output shaft 118 is then coupled to the setscrew 84. While holding the stabilizing handle 120 of the anti-torque component 112 in one hand, the user would then pivot the input handle 114 back and forth using a ratchet-like motion to create torque. The torque created by ratcheting the input handle 114 is conveyed to the output shaft 118 via the transfer mechanism 116. The gear-engagement feature 148 of the input handle 114 interacts with the radial grooves 180 of the gear member 156 such that the gear member 156 is caused to rotate by the ratcheting action of the input handle 114. Because the shear pin 158 is temporarily coupling the gear member 156 and the shearing disk 154, the rotation of the gear member 156 causes rotation of the shearing disk 154, which in turn causes the rotation of the output shaft 118. The rotation of the output shaft 118 consequently causes rotation of the setscrew 84. The setscrew 84 compresses the linking rod 88 into the screw housing 82 of the pedicle screw system 80. This compression will lock the pedicle screw system in place relative to the screw shank 86, thereby providing stabilization to the pedicle screw system 80. The shear pin 158, which serves as a method of torque determination, will shear at the breakaway region 188 once the input torque reaches a predetermined level. The head 182 of the shear pin 158 can be removed by the user and the shaft 186 will drop into the cylindrical cover 190.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternative falling within the spirit and scope of the invention as described herein.

What is claimed is:

1. A system for use in applying torque to a fastener within a housing, comprising:
    a torque input handle;
    an output shaft extending along a longitudinal axis, having an engagement head at the distal end of the output shaft to transfer torque from said input handle to said fastener;
    a transfer mechanism for transferring torque from said input handle to said output shaft; and
    an anti-torque component having an upper portion including a stabilizing handle coupled generally perpendicularly to a lower portion including a cannulated anti-torque element configured to engage said housing within said cannulation.

2. The system for use in applying torque to a fastener of claim 1, wherein said output shaft fits inside of said anti-torque element.

3. The system for use in applying torque to a fastener of claim 1, wherein said anti-torque element includes at least two wings protruding distally from the distal end of said anti-torque shaft that mate with proximally protruding wings of a fastener housing.

4. The system for use in applying torque to a fastener of claim 1, wherein said anti-torque component includes a stabilizing handle having a stabilizing axle which extends generally horizontally into said input handle and about which said input handle rotates.

5. The system for use in applying torque to a fastener of claim 1, wherein said output shaft includes a visual indicator for indicating achievement of a desired amount of torque.

6. The system for use in applying torque to a fastener of claim 5, wherein the visual indicator includes a cylindrical cover having an indicator window.

7. The system for use in applying torque to a fastener of claim 6, wherein said output shaft includes a gear at the proximal end of the output shaft.

8. The system for use in applying torque to a fastener of claim 7, wherein at least one torsion beam extends distally from the gear end of the output shaft through said cylindrical cover, which couples said gear at the proximal end of the output shaft to the rest of the output shaft.

9. The system for use in applying torque to a fastener of claim 7, wherein a torque indicator is coupled to the gear end of the output shaft, which protrudes towards the base surface of said cylindrical cover and twists with the gear.

10. The system for use in applying torque to a fastener of claim 7, wherein the gear end of said output shaft forms a bevel gear with the input handle having a gear at the medial end of the input handle.

11. The system for use in applying torque to a fastener of claim 1, wherein a rod extends generally horizontally from the medial end of said input handle.

12. The system for use in applying torque to a fastener of claim 1, wherein the output shaft includes an inner cylinder.

13. The system for use in applying torque to a fastener of claim 12, wherein a transfer axle fits into said inner cylinder of the output shaft.

14. The system for use in applying torque to a fastener of claim 13, including a shearing disk having an aperture in the general center of said shearing disk to allow insertion of the proximal end of said transfer axle.

15. The system for use in applying torque to a fastener of claim 14, including a rotating gear which fits over the proximal end of said transfer axle and rests on the proximal surface of said shearing disk.

16. The system for use in applying torque to a fastener of claim 15, wherein the shearing disk and rotating gear include co-axial shear pin apertures.

17. The system for use in applying torque to a fastener of claim 16, including a shear pin being inserted through said shearing disk and said rotating gear.

18. A method for applying torque to a fastener within a housing, comprising the following steps:
    (a) coupling the distal end of a stationary cannulated anti-torque device to said housing, said housing being received within the cannulation of said anti-torque device;
    (b) coupling the distal end of an output shaft to the fastener;
    (c) applying force to an input handle; and
    (d) transferring said force to said output shaft.

19. A method as recited in claim 18, wherein the step of applying force to an input handle includes the twisting of the input handle.

20. A method as recited in claim 18, wherein the step of applying force to an input handle includes the use of a rod in a ratcheting motion of the input handle.

* * * * *